United States Patent [19]
Furnish

[11] Patent Number: 5,429,619
[45] Date of Patent: Jul. 4, 1995

[54] SEALING DEVICE FOR ENDOSCOPIC PROBES

[75] Inventor: Greg Furnish, Lawrenceville, Ga.

[73] Assignee: Snowden-Pencer, Inc., Lawrenceville, Ga.

[21] Appl. No.: 183,143

[22] Filed: Jan. 18, 1994

[51] Int. Cl.$^6$ .......................................... A61M 25/00
[52] U.S. Cl. .................. 604/283; 604/264; 604/905
[58] Field of Search .................. 604/280–284, 604/160–169, 158, 905, 264

[56] References Cited

U.S. PATENT DOCUMENTS

| | | | |
|---|---|---|---|
| 5,066,285 | 11/1991 | Hillstead | 604/164 |
| 5,125,904 | 6/1992 | Lee | 604/164 |
| 5,156,596 | 10/1992 | Balbierz et al. | 604/167 X |
| 5,290,244 | 3/1994 | Moonka | 604/158 X |

OTHER PUBLICATIONS

*Surgical Products*, vol. 12, No. 7 (May 1993), col. 3 "High–Volume Irrigation/Suction".
Brochure, Mectra Labs, Inc., "Reddick/Saye Master Lavage" (unknown date).
Brochure, Karl Stortz Endoscopy-America, Inc., "The Nezhat-Dorsey Hydro–Dissection System Ordering Information" Jan. 1993.
Brochure, Cabot Medical, "A Fully Integrated Laparoscopic Irrigation and Instrumentation System" 1991.

*Primary Examiner*—John D. Yasko
*Attorney, Agent, or Firm*—Needle & Rosenberg

[57] ABSTRACT

This invention relates to endoscopic surgical instruments. In particular, the present invention relates to an apparatus for sealing the opening of an endoscopic suction/irrigation valve assembly and probe through which auxiliary endoscopic surgical instruments are inserted. The apparatus provides at least one shaft sealing surface which slidably yet also frictionally grips the shaft of an instrument inserted therethrough to hold the instrument tool at a desired position relative to the tip of the suction/irrigation probe. The invention also provides a means for attaching the sealing member to the valve assembly and a flexible seal radially extending within the lumen of the flexible sealing member for receiving of the instrument therethrough. The flexible seal can be comprised of a plurality of valve leaflets, each of which is independently secured to the luminal surface of the body portion of the sealing member. The valve leaflets can be initially joined along their juxtaposed edges to form a frangible seal such that, when the frangible seal is fractured by insertion of an auxiliary instrument shaft, the leaflets are then move between an open and a normally closed position. These leaflets substantially seal the opening auxiliary instrument opening of the surgical valve assembly and probe during the interchange of auxiliary instruments.

5 Claims, 1 Drawing Sheet

SEALING DEVICE FOR ENDOSCOPIC PROBES

BACKGROUND OF THE INVENTION

1. Field of the Invention

The present invention relates to endoscopic surgical instruments. In particular, the present invention relates to an apparatus for sealing the opening of an endoscopic suction/irrigation valve assembly and probe through which auxiliary endoscopic surgical instruments are inserted. The apparatus provides a shaft sealing surface which also slidably, yet frictionally grips the shaft of an instrument inserted therethrough thereby holding the instrument tool at a desired position relative to the tip of the suction/irrigation probe.

2. Background Art

Endoscopic surgical procedures are rapidly replacing conventional surgical techniques in a variety of applications. Diagnostic or therapeutic endoscopy procedures are generally preferred because they reduce trauma, decrease the risk of infection at incision sites and decrease patient recovery times. Arthroscopy procedures, for example, have all but replaced arthrotomy approaches for joint repair. Likewise, laparoscopic surgery is rapidly becoming the method of choice for a variety of abdominal procedures that once required large laparotomy incisions.

The laparoscope allows the surgeon to perform surgery within the abdomen by providing visualization of an internalized surgical field. The laparoscope and related instruments are usually introduced into the abdomen through a self-sealing cannula introduced into the abdomen via a small incision or trocharized opening in the abdominal wall. These small openings are generally sealed around the cannula during the procedure, thereby preventing airborne contamination of the surgical field and escape of insufflation gases. After surgery, the incision sites are easily closed and usually heal quickly with minimal scarring.

The growing popularity of laparoscopic surgery and the continuing development of new laparoscopic surgical techniques has created a need for specialized surgical instruments. As a result, many surgical instruments have been designed to meet the special needs of the laparoscopic surgeon. Most of these instruments, by necessity, contain certain basic design similarities. For example, in instruments which are comprised of a tool with an articulated member which must be actuated by means located on a handle, the handle is usually connected to the surgical tool via an elongated hollow shaft which contains an actuating rod connecting the tool and actuating means. This elongated shaft design allows the surgical tool to be introduced into the abdomen through the cannula while allowing the surgeon to operate the tool via the actuating means on the handle from a point external of the abdomen. Examples of such instruments include various retractors, hemostats, tissue clamps, needle holders, and the like. Likewise, the tool end of other instruments such as electrocautery electrodes, scalpels, and blunt dissection probes must be connected to the handle via an elongated shaft to enable delivery of the tool to the surgical site.

The need for irrigating and suctioning of the surgical site during surgery led to the development of the endoscopic suction/irrigation probe. This probe is generally a hollow elongated tube, open at both ends, through which irrigation fluid is applied to and suctioned away from the operative site. Typically, the proximal end of the tube is connected to a valve assembly which allows selective operation of an irrigation pump or suctioning vacuum.

Recently, both disposable and non-disposable suction/irrigation probe valve assemblies have been designed which permit an auxiliary instrument, e.g., an electrocautery electrode, to be introduced through the probe via an opening in the valve assembly. When not in use, the opening through which the instruments are introduced is typically sealed with a threaded cap which is screwed into the open end. Instruments which are introduced into the probe normally have a stationary collar positioned on the shaft near the proximal end which is threaded complimentary to the opening on the valve assembly. The collar is positioned on the shaft so that, when inserted into the opening, the instrument tool extends through the distal end of the probe and is exposed at the operative site. Examples of such devices include the NEZFLAT-DORSEY ® HYDRO-DISSECTION ® system developed by American Hydro-Surgical Instruments, Inc. of Delray Beach, Fla.; and the CORSON ® Disposable Suction/Irrigation Probe developed by Cabot Medical Corporation of Langhorne, Pa.

Several major problems exist with this type of suction/irrigation probe and valve assembly design. First, the surgeon must manually remove the screw cap on the valve assembly which seals the auxiliary instrument opening before placing an instrument into the probe. When the cap is removed, the seal of the opening on the valve assembly is lost. This results in a loss of insufflation gases and allows potentially contaminated bodily fluids to escape through the opening under pressure, often directly into the face of the surgeon. The surgeon must quickly re-cap the opening on the valve assembly or screw an auxiliary instrument into the opening to reestablish a seal.

Second, because the threaded collar is secured to the instrument shaft in a fixed position, the surgeon cannot withdraw the instrument tool from the operative site without either unscrewing the instrument or removing the entire probe. Moreover, the probe cannot be utilized for irrigation or suction until the instrument is unscrewed and removed from the valve assembly and the probe.

Third, instruments cannot be interchanged without the time consuming process of unscrewing and removing the first instrument and replacing and screwing in the other instrument. Each time an instrument is interchanged, the seal of the opening on the valve assembly is broken allowing insufflation gases and potentially contaminated bodily fluid to exit the opening under pressure.

A threaded non-disposable Tabb insert has been developed by Cabot Medical Corporation for adaption to the CORSON ® probe to permit introduction of auxiliary instruments into the probe. This insert has several disadvantages, however. First, the probe has to be removed from the operative site before the insert can be applied. Second, the insert does not seal the opening on the valve assembly when there is no instrument inserted through the insert. Therefore, an instrument must either be continually left in the probe or the probe must be withdrawn for replacement of the cap to maintain a seal of the rear opening. Third, the single seal on the collar of the insert often does not adequately seal in the pressurized insufflation gas and irrigating fluids. Therefore, potentially contaminated bodily fluid can squirt around the edges of the seal directly at the surgeon. Fourth, the Cabot insert is non-disposable and is limited in size to 3 mm auxiliary instruments, thereby requiring specially created electrodes and other instruments for use with the insert.

Therefore, there still exists a need in the art for an apparatus which can be easily adapted to the opening on an endoscopic irrigation/suction valve assembly which 1) seals the auxiliary instrument opening when not in use, 2) permits instruments to be easily introduced and/or interchanged while substantially maintaining a seal of the opening during the interchange, 3) adequately seals external surface of the instrument shaft to seal in insufflation gas and irrigation fluid, 4) frictionally yet slidably grips the instrument shaft so as to allow positioning of the instrument tool at any desired location relative to the distal tip of the probe, 5) allows the surgeon to utilize the handle of the valve assembly to maneuver the combination of probe and auxiliary instrument as a single entity, 6) allows use of the irrigation/suctioning capabilities of the probe while an auxiliary instrument is still inserted in the probe, and 7) can be utilized with disposable or non-disposable suction/irrigation probes.

SUMMARY OF THE INVENTION

It is an object of the present invention to provide an apparatus which can be readily adapted to the auxiliary instrument opening on an endoscopic irrigation/suction valve assembly which seals the opening when not in use. It is a further object of the invention to provide an apparatus which permits auxiliary instruments to be easily introduced into the probe and/or interchanged while substantially maintaining a seal of the instrument opening during the interchange.

It is also an object of the present invention to provide an apparatus that forms a seal about external surface of the instrument shaft to seal in insufflation gas and irrigation fluid.

Another object of the present invention is to provide an apparatus that frictionally yet slidably grips and seals about the instrument shaft so as to allow positioning of the instrument tool at any desired location relative to the distal tip of the probe. It is also an object of the invention to provide an apparatus that allows longitudinal movement and axial rotation of the surgical tool within the valve assembly while substantially maintaining the sealing effect of the apparatus.

Accordingly, the present invention provides an apparatus for sealing the rear opening of the auxiliary instrument passage of an endoscopic irrigation/suction surgical valve assembly and probe. The apparatus comprises a flexible sealing member which can be removably attached to the surgical valve assembly having a body portion and a lumen extending longitudinally through the body portion, the lumen being coaxial with the rear opening of the instrument passage of the valve assembly and probe. The lumen has a shaft sealing surface which slidably receives the auxiliary instrument shaft therein and forms a substantially fluid tight seal about the shaft. The shaft sealing surface also frictionally grips the shaft of the instrument at a desired position therealong so as to allow the surgical instrument tool to be maintained at a predetermined position relative to the distal tip of the probe. The firm gripping of the instrument by the apparatus thereby allows the auxiliary instrument and valve assembly to function as a single instrument. The force required to move the auxiliary instrument within the apparatus is greater than the required force to move the probe within the cannula. Therefore, the surgeon can grasp the valve assembly and utilize it as a handle for maneuvering probe and the tooled end of the auxiliary instrument as a single entity.

The invention also provides a means for attaching the sealing member to the valve assembly and a flexible seal radially extending within the lumen of the flexible sealing member for receiving of the instrument therethrough. In one embodiment, the attaching means comprises an adaptor attached to the opening of the valve assembly which is in fluid communication with the instrument passage and probe. The attaching means comprises a portion of the lumen of body portion having a first cavity extending through the distal end that is complimentary to the external surface of the adaptor. The sealing member forms a sealing engagement with the adaptor such that an auxiliary endoscopic surgical instrument can be inserted through the lumen of the sealing member and into the instrument passage of the valve assembly and probe.

In another embodiment, the invention provides a second shaft sealing surface adjacent the proximal end of the sealing member and a second cavity located between the first and second shaft sealing surfaces. The second cavity forms a pressure reducing space which reduces the pressure of fluid which inadvertently escapes past the first shaft sealing surface, thereby augmenting the sealing ability of the second shaft sealing surface.

In one embodiment, the flexible seal is comprised of a plurality of valve leaflets, each of which is independently secured to the luminal surface of the body portion of the sealing member. The valve leaflets are initially joined along their juxtaposed edges to form a frangible seal. When the frangible seal is fractured by insertion of an auxiliary instrument shaft, the leaflets are then moveable between an open and a normally closed position. The leaflets substantially seal the auxiliary instrument opening of the surgical valve assembly and probe during the interchange of auxiliary instruments.

DETAILED DESCRIPTION OF THE INVENTION

Figure 1:
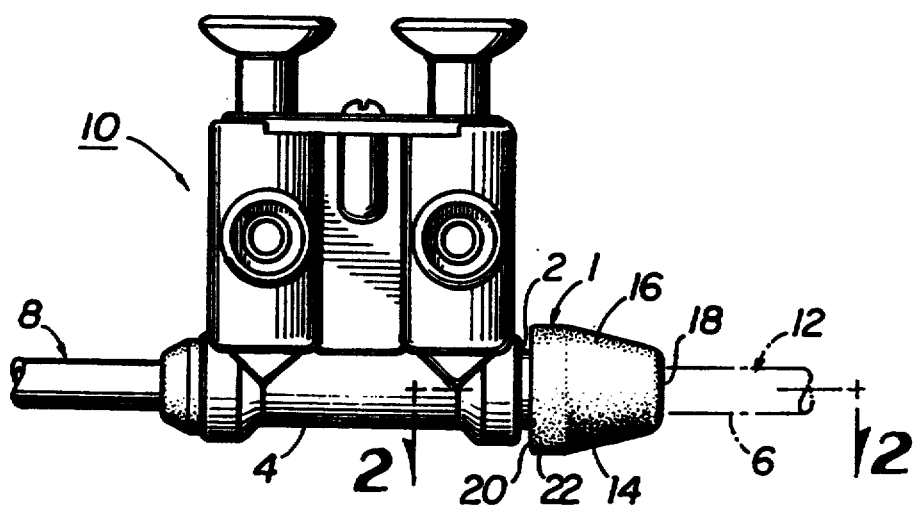
FIG. 1 is a side elevational view of the apparatus attached to a surgical valve assembly.

The present invention may be understood more readily by reference to the following detailed description of specific embodiments and the Examples and Figures included therein.

As used in the claims, "a" means one or more.

It is an object of the present invention to provide an apparatus for sealing the rear opening of the auxiliary instrument passage of an endoscopic irrigation/suction surgical valve assembly and probe. However, the apparatus described herein can be attached to any endoscopic instrument including, but not limited to probes, cannulas, and the like which have a lumen through which a second (or auxiliary) endoscopic instrument may be disposed to provide delivery of the tooled end of the second instrument to an operative site within the body. The auxiliary instrument can be any endoscopic surgical instrument having an elongated shaft with a surgical tool at its operable end. The surgical tool can be any tool routinely used in endoscopic surgery, including, for example, tissue forceps, hemostats, retractors, clamps, scissors, needle holders and drivers, cautery tools and the like. In general, any tool which is attached to an elongated shaft is within the scope of the present invention.

In particular, it is contemplated by the present invention that the apparatus described herein is suitable for direct attachment to the proximal end of any endoscopic surgical irrigation or suction (aspiration) probe, or to the auxiliary instrument opening of the valve assembly to which the probe is attached, or preferably to an adaptor which is attached to the valve assembly. By proximal end is meant the end nearest to the surgeon during normal use of the instrument. The valve assembly can be any of the well known configurations known to the art, including, e.g., trumpet, valves, slide valves, tube crimping valves and rotary valves.

Typically, the trumpet-type valve assembly has an opening on its rear or proximal end into an instrument passage which runs through the body portion of the valve assembly and which is coaxial with the lumen of the suction/irrigation probe. The present invention is designed to be removably attached to the rear opening of the valve assembly such that a second or auxiliary endoscopic surgical instrument of the type described above can be readily introduced into and removed from the instrument passage of the valve assembly and probe via the rear opening.

The present invention can be constructed from any suitable material including, but not limited to elastomeric plastics, and synthetic and natural rubbers. In the presently preferred embodiment, the apparatus is disposable and is constructed from a silicon rubber. Briefly, the apparatus can be constructed by utilizing a multiple cavity compression or transfer mold that is split along its axial length to form two halves. Two inserts, which form the internal structure of the device, are inserted into each cavity of the mold and the halves closed. Synthetic thermoset silicone rubber is then placed within each cavity and cured to form the apparatus.

Figure 2:
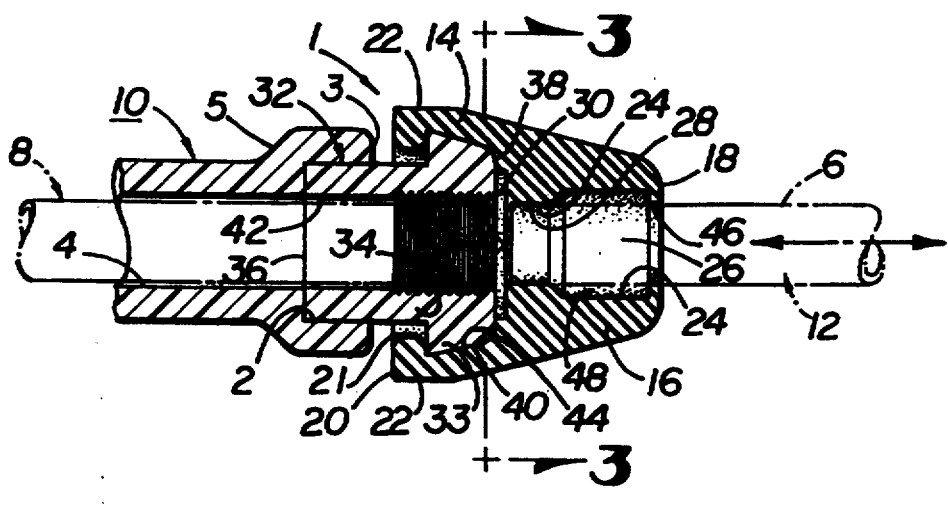
FIG. 2 is a longitudinal cross-section of the apparatus taken along lines 2—2 in FIG. 1.

Referring now to FIG. 1 and FIG. 2, the present invention provides an apparatus 1 for sealing the rear opening 2 of an instrument passage 4 of an endoscopic irrigation/suction surgical valve assembly 10 and suction/irrigation probe 8. In the embodiment shown in FIG. 1, the valve assembly 10 has a rear opening 2, such that the apparatus 1, when attached to the rear opening 2, allows an endoscopic surgical instrument 6 of the type having an elongated shaft 12 with a surgical tool (not shown) at its operable (distal) end to be readily introduced into and removed from the instrument passage 4 of the valve assembly 10 via the rear opening 2 formed in the rear face 3. Adjacent the rear face 3 on assembly 10 is an enlarged portion 5.

The apparatus 1 is comprised of a flexible sealing member 14 which can be removably attached to the surgical valve assembly 10. The flexible sealing member 14 has a body portion 16 comprised of a proximal end 18, an opposite distal end 20, an outer surface 22, a luminal surface 24 and a lumen 26 longitudinally extending through the body portion 16 of the sealing member 14 and interconnecting the proximal and distal ends 18, 20. As described more in detail below, the invention also provides a means 32 for attaching the flexible sealing member 14 to the valve assembly 10 and a flexible seal 30 integrally formed and radially extending within the lumen 26 for receiving the instrument therethrough. As shown in FIGS. 1 and 2, the apparatus is configured such that when attached to the rear opening 2 of the valve assembly 10, the lumen 26 of the flexible sealing member 14 is coaxially aligned with the rear opening 2 and the instrument passage 4 of the valve assembly 10.

The lumen 16 of the flexible sealing member 14 has a first shaft sealing surface 28 of a first diameter which extends along at least a portion of the lumen 26 adjacent the seal 30. The dimension of the first diameter can vary depending upon the shaft diameter of the auxiliary instruments which are to be inserted therethrough. The dimension of the first diameter can also vary depending on the choice of materials utilized in construction of the apparatus 1. For instance, in the presently preferred embodiment, as mentioned above, the apparatus 1 is constructed from an elastically deformable material such as silicone, with the diameter of the first shaft sealing surface 28 being configured to be smaller than the diameter of the auxiliary instrument shaft. For example, if the shaft diameter of the auxiliary instruments is about 5 mm, then the first diameter of the first shaft sealing surface 28 could be between about 3.60 mm and 3.86 mm, but especially about 3.73 mm. Therefore, the first shaft sealing surface 28 grips and seals around the exterior surface of the instrument shaft 12 because the sealing surface 28 expands around and exerts a force upon the shaft 12 as the instrument 6 is inserted therethrough. The width along the longitudinal axis (thickness) of the first shaft sealing surface 28 is generally about 80-90/1000th inches thick, but can vary depending upon the specific embodiment.

The first shaft sealing surface 28 forms a substantially fluid tight seal around the shaft 12 and slidably, yet frictionally, grips about the shaft 12 of the instrument 6 at any desired position therealong so as to allow the surgical instrument tool (not shown) to be maintained at a predetermined position. The predetermined position refers to the position of the surgical tool relative to the distal tip of the suction irrigation probe 8 and can include any position of the tool, up to and including complete insertion or complete withdrawal of the instrument 6 from the valve assembly 10 and probe 8. The predetermined position can be selected by the surgeon depending upon his or her need for a particular application. By "substantially fluid tight seal" is meant that the sea prevents escape of between about 99% and 100% of the bodily fluids, irrigation liquids and or insufflation gases that are under pressure from escaping from the body cavity, e.g., the abdomen, where the operative site and hence the tip of the probe 8 is located.

For example, when the instrument 6 is fully inserted into the probe 8, the surgical tool (not shown) extends past the distal tip of the probe 8 to allow utilization of the tool at the operative site. The firm grip on the instrument shaft 12 provided by the first shaft sealing surface 28 allows the probe and auxiliary instrument to move within the endoscopic cannula and function as a single instrument, i.e., the force needed to move the probe in and out of the cannula is slightly less than the force needed to move the auxiliary instrument in and out of the apparatus 1. The surgeon can maneuver the surgical tool by utilizing the body portion of the valve assembly 10 as a handle.

Additionally, by retracting the instrument 6 proximally, the surgeon can position the tool at any desired location within the shaft of the probe 8 and the instrument 6 will be held in position by the first shaft sealing surface 28 of apparatus 1. Retraction of the auxiliary instrument 6 proximally so that the tool is proximal to the distal tip of the probe 8 allows the surgeon to suction/irrigate with the probe 8 without having to remove the instrument 6 from the valve assembly 10.

As stated above, the apparatus 1 can be attached directly to the suction/irrigation probe, directly to the rear opening 2 of the valve assembly 10 or to an adaptor 32 as is depicted in FIG. 2. In the embodiment shown in FIG. 2, the attaching means comprises an adaptor 32 having a body portion 34, a first end 36, an opposite second end 38 having an external surface 40 and a bore 42 longitudinally extending through the body portion 34 of the adaptor 32. The first end 36 of the adaptor 32 is capable of being removably received within the rear opening 2 of a valve assembly 10. It is contemplated that the first end 36 of the adaptor 32 can be of any shape and configuration that is necessary to compliment a particular valve assembly design. The second end 38 of the adaptor 32 can removably engage the distal end 20 of the sealing member 14, such that the adaptor bore 42 is coaxial with and in fluid communication with the auxiliary instrument passage 4 of the valve assembly 10 and probe 8.

Still referring to the embodiment shown in FIG. 2, the attaching means can further comprise a portion of the lumen 26 of the body portion 34 having a first cavity 44 extending through the distal end 20, the first cavity 44 being shaped complimentary to the enlarged external surface 40 of the adaptor 32 adjacent second end 38. The first cavity 44 is designed to sealingly receive the adaptor 32 therein such that an auxiliary endoscopic surgical instrument 6 can be inserted through the lumen 26 of the sealing member 14 and into the instrument passage 4 of the valve assembly 10. The male-female configuration of the attaching means shown in FIG. 2 allows the sealing member 14 to be quickly and easily attached to and removed from the adaptor 32. In one embodiment, the disposable sealing member 14 is constructed from a molded elastomeric plastic or rubber. The distal end 20 has an inwardly directed ring 21 which can be snap-fitted over the male head 33 of the adaptor 32 to securely maintain the attachment of the sealing member 14 to the adaptor 32.

In addition to the complimentary male-female configuration of the second end 38 and the first cavity 44 respectively, one can appreciate the many other complimentary configurations or methods which can be utilized as the attaching means for affixing the apparatus 1 to the valve assembly 10 and/or to the probe 8. It is contemplated by the invention that, e.g., adhesive mountings can also be utilized as the attaching means.

An additional mode of attachment of apparatus 1 to assembly 10 is to have the flexible sealing member receive therein the enlarged portion 5 of the assembly 10, thus eliminating the adaptor 32.

Figure 3:
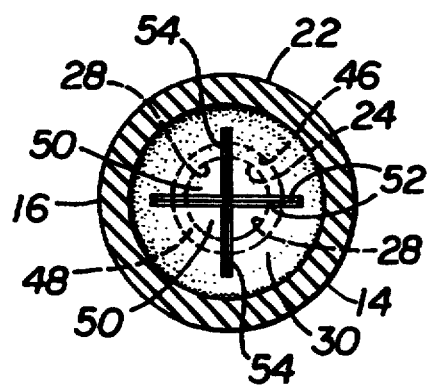
FIG. 3 is a cross-section of the apparatus taken along lines 3—3 in FIG. 2.

Referring now to FIGS. 2 and 3, one embodiment of the invention provides the apparatus 1 wherein the lumen 26 of the body portion 16 further comprises a second shaft sealing surface 46 adjacent the proximal end 18 and a second cavity 48 located between the first and second shaft sealing surfaces 28, 46. The second cavity 48 preferably has a second diameter larger than the first diameter of the first shaft sealing surface 28. The second shaft sealing surface 46 has a third diameter that is substantially similar (i.e., preferably the same or a slightly smaller diameter) to the first diameter of the first shaft sealing surface 28, such that the second shaft sealing surface 46 also frictionally grips and allows slidable engagement of the shaft 12 of the endoscopic surgical instrument 6 inserted therethrough. For example, for auxiliary instruments with a shaft diameter of about 5 mm, the diameter of the second shaft sealing surface 46 can be between about 3.17 mm and 3.43 mm but especially about 3.30 mm. The thickness of the seal is generally about 20/1000th inches thick, but can vary depending upon the particular embodiment.

The sealing capability of second shaft sealing surface 46 is augmented by the second cavity 48 which acts as a pressure reducing chamber for any fluids which may inadvertently escape from the substantial seal formed by the first shaft sealing surface 28. The pressure reducing chamber formed by the larger diameter second cavity 48 is defined longitudinally between the first and second shaft sealing surfaces 28, 46. In essence, the second shaft sealing surface 46 acts in conjunction with the first shaft sealing surface 28 and the second cavity 48 to provide a fluid tight seal during reciprocal movement of the instrument shaft 12 within the body portion 16 of the apparatus 1.

In the presently preferred embodiment of the apparatus 1 shown in FIGS. 2 and 3, the flexible seal 30 is comprised of a plurality of valve leaflets 50, each of which is independently secured to the luminal surface of the body portion 16. The valve leaflets 50 are initially joined along their juxtaposed edges 52 to form a frangible seal having fracture lines 54 which, when torn by the insertion of an auxiliary instrument 6 therethrough, allows the leaflets 50 to move from a normally closed position to an open position. In one embodiment, the flexible seal 30 and valve leaflets 50 are about 40/1000th inches thick, whereas the fracture lines 54 are about 10/1000th inches thick.

Prior to the insertion of any auxiliary instrument into the apparatus 1, the flexible seal 30 completely seals the rear opening 2 of the instrument passage 4, valve assembly 10 and probe 8. After removal of an auxiliary instrument from the instrument passage 4, the valve leaflets 50 move to the normally closed position and substantially seal the rear opening 2 of the surgical valve assembly 10 from the external environment as well as providing a substantially fluid tight seal against escape of bodily fluids, irrigation liquids, and/or insufflation gases from the rear opening 2 of the valve assembly 10. The valve leaflets 50 are moveable to an open position when a surgical instrument 6 is inserted into the apparatus 1 to sealingly engage the exterior circumference of the instrument shaft 12.

What is claimed is:

1. An apparatus for sealing the rear opening of an auxiliary instrument passage of an endoscopic irrigation/suction surgical valve assembly and probe, such that said apparatus, when attached to the rear opening of said valve assembly, allows an endoscopic surgical instrument of the type having an elongated shaft with a surgical tool at its operable end to be introduced into and removed from the auxiliary instrument passage of the valve assembly via the rear opening, comprising:

a. a flexible sealing member which can be removably attached to said surgical valve assembly, said sealing member having a body portion comprised of a proximal end, an opposite distal end, an outer surface, a luminal surface and a lumen longitudinally extending through the body portion and interconnecting the proximal and distal ends, the lumen being coaxial with said rear opening of said instrument passage of said valve assembly, said lumen having a first shaft sealing surface of a first diameter extending along at least a portion of the lumen which is adapted to receive the shaft slidingly therealong and which forms a substantially fluid tight seal about the shaft, said first shaft sealing is adapted to frictionally grip the shaft of said instrument at a desired position therealong so as to allow the surgical instrument tool to be maintained at a predetermined position;

b. means for attaching said sealing member to said valve assembly; and c. a flexible seal radially extending within said lumen for receiving said instrument therethrough.

2. The apparatus of claim 1, wherein said attaching means comprises an adaptor having a body portion, a first end, an opposite second end having an external surface and a bore longitudinally extending through the body portion of said adaptor, the first end being received within the rear opening of said valve assembly, and the second end being in engagement with the distal end of said sealing member, such that the bore is in fluid communication with the auxiliary instrument passage of said valve assembly.

3. The apparatus of claim 2, wherein said attaching means further comprises a portion of the lumen of the body portion of said sealing member having a first cavity extending through the distal end, said first cavity being shaped complimentary to the external surface of said adaptor for sealingly engaging said adaptor such that an endoscopic surgical instrument can be inserted through the lumen of said sealing member and into the instrument passage of said valve assembly.

4. An apparatus for sealing the rear opening of an auxiliary instrument passage of an endoscopic irrigation/suction surgical valve assembly and probe, such that said apparatus, when attached to the rear opening of said valve assembly, allows an endoscopic surgical instrument of the type having an elongated shaft with a surgical tool at its operable end to be introduced into and removed from the auxiliary instrument passage of the valve assembly via the rear opening, comprising:

a. a flexible sealing member which can be removably attached to said surgical valve assembly, said sealing member having a body portion comprised of a proximal end, an opposite distal end, an outer surface, a luminal surface and a lumen longitudinally extending through the body portion and interconnecting the proximal and distal ends, the lumen being coaxial with said rear opening of said instrument passage of said valve assembly, said lumen having i) a first shaft sealing surface of a first diameter extending along at least a portion of the lumen which is adapted to receive the shaft slidingly therealong and which forms a substantially fluid tight seal about the shaft, said first shaft sealing surface is adapted to frictionally gripping the shaft of said instrument at a desired position therealong so as to allow the surgical instrument tool to be maintained at a predetermined position and ii) a second shaft sealing surface adjacent the proximal end and a second cavity located between the first and second shaft sealing surfaces, said second cavity having a second diameter larger than the first diameter and said second shaft sealing surface having a third diameter substantially similar to the first diameter, such that said second shaft sealing surface is adapted to frictionally grips and allows slidable engagement of the shaft of said endoscopic surgical instrument so as to provide a substantially fluid tight seal during reciprocal movement of said instrument shaft therein, the larger diameter second cavity thereby forming a pressure reducing space defined longitudinally between the first and second shaft sealing surfaces;

b. means for attaching said sealing member to said valve assembly; and c. a flexible seal radially extending within said lumen for receiving said instrument therethrough.

5. The apparatus of claim 1, wherein said flexible seal is comprised of a plurality of valve leaflets, each of which is independently secured to the luminal surface of said body portion and initially joined along their juxtaposed edges to form a frangible seal which, when fractured by insertion of the instrument shaft therethrough, allows the leaflets to move between a normally closed position so as to substantially seal the rear opening of said surgical valve assembly from an external environment and an open position when the surgical instrument is inserted therethrough to sealingly engage thereabout the exterior circumference of said instrument shaft.

* * * * *